United States Patent [19]

Bengmark et al.

[11] Patent Number: 4,533,356
[45] Date of Patent: Aug. 6, 1985

[54] SURGICAL DEVICE

[75] Inventors: Stig Bengmark, Lund; Albert Broomé, Helsingborg, both of Sweden; Christian H. Overland, Hundested, Denmark

[73] Assignee: Uno Plast A/S, Hundested, Denmark

[21] Appl. No.: 201,062

[22] PCT Filed: Dec. 12, 1979

[86] PCT No.: PCT/DK79/00058
§ 371 Date: Aug. 12, 1980
§ 102(e) Date: Aug. 12, 1980

[87] PCT Pub. No.: WO80/01239
PCT Pub. Date: Jun. 26, 1980

[30] Foreign Application Priority Data

Dec. 12, 1978 [DK] Denmark ............................. 5581/78

[51] Int. Cl.³ .............................................. A61F 13/00
[52] U.S. Cl. .................................. 604/358; 604/385 R; 128/3
[58] Field of Search .............. 128/296, 292, 350 R, 128/285, 290 R, 3; 604/358, 385

[56] References Cited

U.S. PATENT DOCUMENTS

| 810,117 | 1/1906 | Green . | |
| 3,324,855 | 6/1967 | Heimlich | 128/296 X |
| 3,563,243 | 2/1971 | Lindquist | 128/287 |
| 3,570,493 | 3/1971 | Olsson | 128/290 |
| 3,706,311 | 12/1972 | Kokx et al. | 128/285 |
| 3,823,720 | 7/1974 | Tribble | 128/350 R |
| 3,834,390 | 9/1974 | Hirsch | 128/296 |
| 3,923,052 | 12/1975 | Zoephel | 128/132 D |
| 3,935,863 | 2/1976 | Kliger | 128/296 |
| 3,971,378 | 7/1976 | Krantz | 128/285 |
| 4,055,184 | 10/1977 | Karami | 128/287 |

FOREIGN PATENT DOCUMENTS

| 1022353 | 6/1958 | Fed. Rep. of Germany | 128/296 |
| 2823562 | 1/1979 | Fed. Rep. of Germany | 128/296 |

*Primary Examiner*—Michael H. Thaler
*Attorney, Agent, or Firm*—Watson, Cole, Grindle & Watson

[57] ABSTRACT

A rod-shaped device for internal use in connection with operations in body cavities and comprising a non-elastically deformable, flexible member surrounded by a soft liquid absorbing material which optionally is enclosed in an overwrap.

10 Claims, 3 Drawing Figures

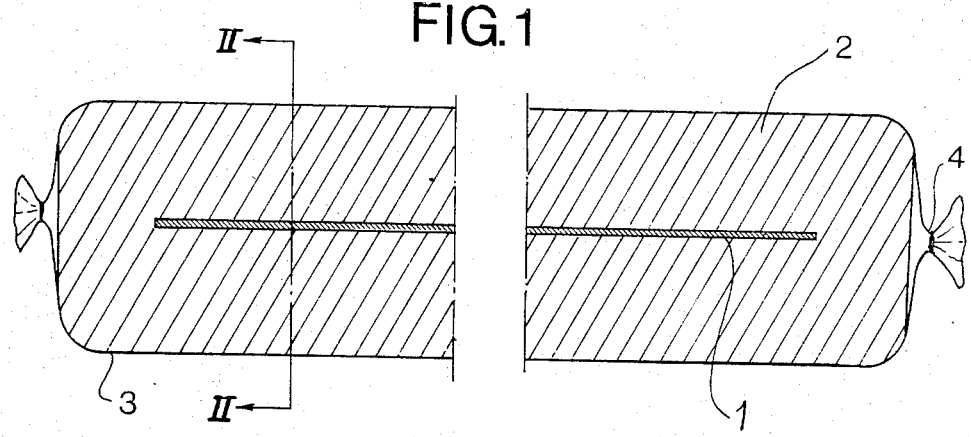
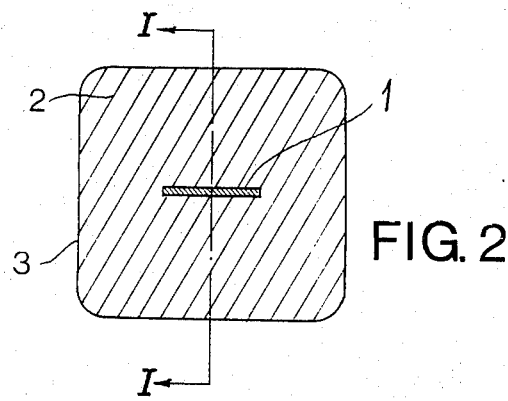

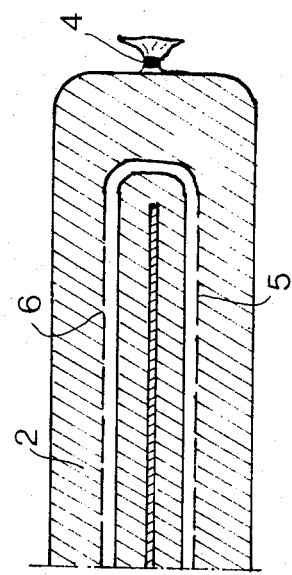
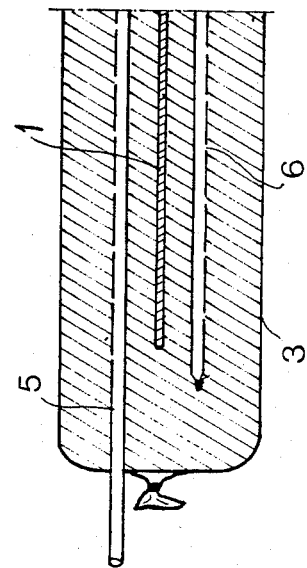
FIG.3

SURGICAL DEVICE

TECHNICAL FIELD

This invention relates to a surgical device for internal use during surgical operations in body cavities, particularly during abdominal operations.

BACKGROUND ART

During abdominal operations it is ordinarily necessary to push the gastrointestinal canal aside to keep the place at which the operation is performed free and easily accessible. With this end in view, it is well known to maintain the intestines in a fixed position by utilizing liquid-absorbing cotton sheets and wound retractors which are manually held during the operation by one or more nurses assisting the surgeon.

The use of such cotton sheets and wound retractors present several drawbacks. Thus, the use of cotton sheets does not prevent the retracted intestines from being gradually released and causing inconvenience to the surgeon because the assistants gradually get tired of holding the cotton sheets and wound retractors or because the cotton sheets, due to their limited liquid absorption capacity, from time to time have to be replaced with new cotton sheets. The replacement of the cotton sheets not only delays the surgical operation but may also result in the operation is not performed at the most suitable time.

Furthermore, small particles may be released from the cotton sheets into the body cavity, which are then difficult to remove.

The object of the present invention is to provide a surgical device for use in body cavities and for maintaining organs, such as intestines, in a fixed position during an operation without the aid of assisting personnel and without damaging the organs.

SUMMARY OF THE INVENTION

This object is attained by the surgical device of the invention, this device being rod-shaped and comprising a non-elastically deformable, flexible member surrounded by a soft, liquid-absorbing material which is optionally is enclosed in an overwrap.

The presence of the non-elastically deformable, flexible member in the surgical device of the invention has the effect that the rod-shaped device, after being suitably shaped to keep organs, such as intestines, in a given position, maintains the shape thus imparted to it, thus making manually held devices superfluous. Since the non-elastically deformable member is surrounded by the soft liquid-absorbing material, the bending of the device around the organs will cause no damage to them.

The presence of the liquid-absorbing material also has the effect that exuded liquid, such as blood, is collected and is prevented from interfering with the operation.

In view of the fact that the thickness of the liquid-absorbing material surrounding the non-elastically deformable member can be varied without any significant adverse effect on the flexibility of the device of the invention, the liquid absorption capacity of the device may be varied within wide ranges and as required.

A high liquid absorption capacity of the device of the invention may be of vital importance for a successful operation. Thus, in case the patient loses blood during the operation, the blood is absorbed in the liquid-absorbing material and the amount of blood lost can be measured at intervals by withdrawing the device from the body cavity and removing the blood therefrom by squeezing. By determining the amount of blood lost, the anaesthetic can be more correctly dosed because the dosage of anaesthetic depends on the remaining amount of blood in the patient.

A preferred embodiment of the invention comprises a perforated, flexible tube incorporated in the liquid-absorbing material and adapted to be connected to a suction device, e.g. a pump, via a liquid collector.

When using this embodiment of the surgical device of the invention, the blood absorbed in the liquid-absorbing material can be continuously removed therefrom and collected in the liquid collector, thus permitting the amount of blood lost to be continuously recorded.

U.S. Pat. No. 3,923,052 discloses a fenestrated surgical drape comprising one or more sheets of a non-woven material and strips of a non-elastic deformable, flexible material. The purpose of the strips is to conform the drape to the shape of the body around the place at which the surgical incision is to be made. Thus this prior art drape is intended for external use and has a low absorption capacity.

The non-elastically deformable member of the surgical device of the invention is preferably metallic, e.g. made from aluminum. A metallic member presents the special advantage that it can be located by X-ray examination if it has been unintentionally left in a body cavity.

The shape of the non-elastically deformable member is not critical, but it is preferably in the shape of a strip.

It is to be understood that the non-elastically deformable member, may be an articulated member provided the joints are constructed in a manner such that the member maintains its shape after being deformed.

The liquid-absorbing material preferably consists of soft plastic foam, e.g. polyether foam. By using soft polyether foam, liquid absorbed therein can be easily removed therefrom by compression and the device can be re-used in the same operation.

Also other liquid absorbing materials, e.g. cotton wool and similar materials, are suitable. In case the liquid-absorbing material is cotton wool, it is particularly preferable to use an overwrap, e.g. an overwrap prepared from a non-fluffy plastic material. Thus, the overwrap may be tubular and may be woven or knitted. It is preferably prepared from a plastic matrial, e.g. nylon yarn.

The tubular overwrap may be closed at its ends by well known methods, such as tying, gluing, sewing or sealing.

BRIEF DESCRIPTION OF DRAWINGS

FIG. 1 is a sectional view of a preferred embodiment of the surgical device of the invention, taken along line I—I in FIG. 2, FIG. 2 is a sectional view of the device illustrated in FIG. 1 and taken along line II—II in FIG. 1, FIG. 3 is a longitudinal sectional view of another embodiment of the device of the invention.

DETAILED DESCRIPTION OF THE PEFERRED EMBODIMENTS

FIGS. 1 and 2 show a metallic strip 1 incorporated in a rod-shaped member 2 of polyether foam. The rod-shaped member 2 is surrounded by an overwrap 3 consisting of a woven nylon tube. The nylon tube comprises closures 4 at its ends, these closures being obtained by tying. The metal strip 1 may be an aluminum strip having a thickness of about 1 mm and a width of about 15 mm. The polyether foam block may have a weight of 20 kg/m$^3$ and cross sectional dimensions of 45.45 mm. The length of the device illustrated may vary within wide ranges.

FIG. 3 illustrates a device corresponding to that of FIGS. 1 and 2 except that it additionally comprises a plastic tube 5 having perforations 6 incorporated in the block 2 of polyether foam.

The plastic tube 5 is closed at one end 7 and the other end is adapted to be connected with a suction device (not shown), e.g., a pump, via a liquid collector (not shown).

We claim:

1. A surgical device for holding internal body parts in place during surgical operations in body cavities and which, once bent into a desired shape, will retain the desired shape, the surgical device comprising
    a rod-shaped member, said rod-shaped member being composed of a soft, liquid-absorbing material,
    a non-elastically deformable, flexible member embedded in said rod-shaped member, and
    an overwrap means surrounding said rod-shaped member.

2. The surgical device as defined in claim 1 wherein said rod-shaped member is composed of cotton wool.

3. The surgical device as defined in claim 1 wherein said rod-shaped member is composed of plastic foam.

4. The surgical device as defined in claim 3 wherein said plastic foam is polyether foam.

5. The surgical device as defined in claim 1 wherein said non-elastically deformable, flexible member is composed of a metallic material.

6. The surgical device as defined in claim 5 wherein said metallic material is aluminum.

7. The surgical device as defined in claim 1 wherein said non-elastically deformable, flexible member is strip shaped.

8. The surgical device as defined in claim 1 wherein a perforated tube is additionally embedded in said rod-shaped member.

9. The surgical device as defined in claim 8 wherein one end of said perforated tube extends outwardly of said rod-shaped member and through an opening in said overwrap means.

10. The surgical device as defined in claim 1 wherein said overwrap means is in the form of a woven nylon tube which is closed at its ends.

* * * * *